(12) United States Patent
Derowe et al.

(10) Patent No.: US 12,708,317 B2
(45) Date of Patent: Aug. 18, 2026

(54) ELECTROPHYSIOLOGICAL DEVICE AND METHOD FOR DIAGNOSIS OF ACUTE UNILATERAL OTITIS MEDIA (AOM)

(71) Applicants: RAMOT AT TEL-AVIV UNIVERSITY LTD., Tel-Aviv (IL); ICHILOV TECH LTD., Tel Aviv (IL)

(72) Inventors: Ari Derowe, Tel Aviv (IL); Tal Yehuda Barkai, Tel Aviv (IL); Linor Klein, Tel Aviv (IL); Mickey Scheinowitz, Tel Aviv (IL); Amir Dagan, Tel Aviv (IL)

(73) Assignees: RAMOT AT TEL-AVIV UNIVERSITY LTD., Tel-Aviv (IL); ICHILOV TECH LTD., Tel Aviv (IL)

( * ) Notice: Subject to any disclaimer, the term of this patent is extended or adjusted under 35 U.S.C. 154(b) by 329 days.

(21) Appl. No.: 18/283,085

(22) PCT Filed: Mar. 24, 2022

(86) PCT No.: PCT/IL2022/050329
§ 371 (c)(1),
(2) Date: Sep. 20, 2023

(87) PCT Pub. No.: WO2022/201163
PCT Pub. Date: Sep. 29, 2022

(65) Prior Publication Data

US 2024/0164696 A1 May 23, 2024

Related U.S. Application Data

(60) Provisional application No. 63/165,836, filed on Mar. 25, 2021.

(51) Int. Cl.
*A61B 5/383* (2021.01)
*A61B 5/00* (2006.01)
(Continued)

(52) U.S. Cl.
CPC .............. *A61B 5/383* (2021.01); *A61B 5/291* (2021.01); *A61B 5/372* (2021.01); *A61B 5/381* (2021.01);
(Continued)

(58) Field of Classification Search
CPC ............ A61B 2018/1253; A61B 5/388; A61B 5/4017; A61B 5/6817; A61B 5/682;
(Continued)

(56) References Cited

U.S. PATENT DOCUMENTS

2016/0022167 A1 1/2016 Simon
2020/0363871 A1 11/2020 Vu et al.
2021/0169404 A1* 6/2021 Chaturvedi ........... A61M 21/00

OTHER PUBLICATIONS

Enger, Comprehensive Recordings of Taste Function in Patients with Dysgeusia, Jun. 2017 (Year: 2017).*
(Continued)

*Primary Examiner* — Gerald Johnson
(74) *Attorney, Agent, or Firm* — The Roy Gross Law Firm, LLC; Roy D. Gross

(57) ABSTRACT

Systems and methods for diagnosis of Acute Otitis Media (AOM) with a monopolar probe in a territory innervated by a chorda tympani nerve (CTN) by applying a stimulus by the monopolar, measuring a response to the stimulus, changing the strength of the stimulus applied based on the measured response until the measured response reaches a threshold value, determining a first stimulus strength at the threshold value, repeating these steps for another predefined location in a territory innervated by the CTN associated with a second ear, to determine a second stimulus strength at the threshold value for the second predefined location; and diagnosing AOM based on a difference between the determined first and second stimulus strengths for the first and second locations.

15 Claims, 6 Drawing Sheets

(51) Int. Cl.

| | |
|---|---|
| ***A61B 5/291*** | (2021.01) |
| ***A61B 5/372*** | (2021.01) |
| ***A61B 5/381*** | (2021.01) |
| *A61B 5/05* | (2021.01) |
| *A61B 5/12* | (2006.01) |
| *A61B 5/31* | (2021.01) |
| *A61B 5/388* | (2021.01) |
| *A61N 1/05* | (2006.01) |
| *A61N 1/18* | (2006.01) |
| *A61N 1/36* | (2006.01) |

(52) U.S. Cl.

CPC .............. *A61B 5/682* (2013.01); *A61B 5/004* (2013.01); *A61B 5/0048* (2013.01); *A61B 5/0082* (2013.01); *A61B 5/0084* (2013.01); *A61B 5/0088* (2013.01); *A61B 5/05* (2013.01); *A61B 5/126* (2013.01); *A61B 5/31* (2021.01); *A61B 5/388* (2021.01); *A61B 5/4017* (2013.01); *A61B 5/4836* (2013.01); *A61B 5/68* (2013.01); *A61B 5/6813* (2013.01); *A61B 5/6817* (2013.01); *A61B 2503/06* (2013.01); *A61N 1/0548* (2013.01); *A61N 1/18* (2013.01); *A61N 1/36031* (2017.08)

(58) Field of Classification Search

CPC ....... A61B 5/381; A61B 5/383; A61B 5/0088; A61N 1/0548

See application file for complete search history.

(56) References Cited

OTHER PUBLICATIONS

Banerjee, Development of an Automated Electrogustometer, Jan. 2011 (Year: 2011).*

Loudon et al., Behavior Research Methods, Instruments, & Computers, 1997 (Year: 1997).*

Gudziol H, Guntinas-Lichius O. Electrophysiologic assessment of olfactory and gustatory function. Handb Clin Neurol. 2019;164:247-262. doi: 10.1016/B978-0-444-63855-7.00016-2. PMID: 31604551.

Ohla K, Hudry J, le Coutre J. The cortical chronometry of electrogustatory event-related potentials. Brain Topogr. Sep. 2009;22(2):73-82. doi: 10.1007/s10548-009-0076-7. Epub Feb. 6, 2009. PMID: 19199019.

Sano M, Ito K, Suzukawa K, Kaga K, Yamasoba T. Influence of chronic middle ear diseases on gustatory function: an electrogustometric study. Otol Neurotol. Jan. 2007;28(1):44-7. doi: 10.1097/01.mao.0000244359.49756.a3. PMID: 17195745.

Hing E, Cherry DK, Woodwell DA. National Ambulatory Medical Care Survey: 2004 summary. Adv Data. Jun. 23, 2006;(374):1-33. PMID: 16841616.

Vergison A, Dagan R, Arguedas A, Bonhoeffer J, Cohen R, Dhooge I, Hoberman A, Liese J, Marchisio P, Palmu AA, Ray GT, Sanders EA, Simões EA, Uhari M, van Eldere J, Pelton SI. Otitis media and its consequences: beyond the earache. Lancet Infect Dis. Mar. 2010;10(3):195-203. doi: 10.1016/S1473-3099(10)70012-8. PMID: 20185098.

Bluestone CD. Clinical course, complications and sequelae of acute otitis media. Pediatr Infect Dis J. May 2000;19(5 Suppl):S37-46. doi: 10.1097/00006454-200005001-00007. PMID: 10821471.

Elliott CA, Zalzal GH, Gottlieb WR. Acute otitis media and facial paralysis in children. Ann Otol Rhinol Laryngol. Jan. 1996;105(1):58-62. doi: 10.1177/000348949610500110. PMID: 8546426.

Joseph EM, Sperling NM. Facial nerve paralysis in acute otitis media: cause and management revisited. Otolaryngol Head Neck Surg. May 1998;118(5):694-6. doi: 10.1177/019459989811800525. PMID: 9591875.

Ylikoski J, Gamoletti R, Galey F. Chorda tympani nerve fibers in man. Acta Otolaryngol. Mar.-Apr. 1983;95(3-4):291-6. doi: 10.3109/00016488309130945. PMID: 6837282.

Andrews JC, Abemayor E, Alessi DM, Canalis RF. Parotitis and facial nerve dysfunction. Arch Otolaryngol Head Neck Surg. Feb. 1989;115(2):240-2. doi: 10.1001/archotol.1989.01860260114026. PMID: 2914097.

Shin IH, Park DC, Kwon C, Yeo SG. Changes in taste function related to obesity and chronic otitis media with effusion. Arch Otolaryngol Head Neck Surg. Mar. 2011;137(3):242-6. doi: 10.1001/archoto.2011.23. PMID: 21422307.

Leung RM, Ramsden J, Gordon K, Allemang B, Harrison BJ, Papsin BC. Electrogustometric assessment of taste after otologic surgery in children. Laryngoscope. Oct. 2009;119(10):2061-5. doi: 10.1002/lary.20588. PMID: 19598212.

Tomita H, Ikeda M, Okuda Y. Basis and practice of clinical taste examinations. Auris Nasus Larynx. 1986;13 Suppl 1:S1-15. doi: 10.1016/s0385-8146(86)80029-3. PMID: 3767768.

Walliczek-Dworschak U, Knauer CM, Murbe D, Mainka A, Hummel T. Analysis of taste function in patients before and after cochlear implant surgery. Rhinology. Jun. 1, 2018;56(2):149-154. doi: 10.4193/Rhin17.178. PMID: 29306957.

Saito T, Ito T, Ito Y, Yamada T, Okamoto M, Manabe Y. Gustatory Dysfunction and Decreased Number of Fungiform Taste Buds in Patients With Chronic Otitis Media With Cholesteatoma. Ann Otol Rhinol Laryngol. Sep. 2016;125 (9):704-9. doi: 10.1177/0003489416646793. Epub May 2, 2016. PMID: 27141029.

Berling Holm K, Bornefalk-Hermansson A, Knutsson J, von Unge M. Surgery for Chronic Otitis Media Causes Greater Taste Disturbance Than Surgery for Otosclerosis. Otol Neurotol. Jan. 2019;40(1):e32-e39. doi: 10.1097/MAO.0000000000002048. PMID: 30540698.

Fogel A, Blissett J. Associations between Otitis media, taste sensitivity and adiposity: Two studies across childhood. Physiol Behav. Sep. 1, 2019;208:112570. doi: 10.1016/j.physbeh.2019.112570. Epub Jun. 5, 2019. PMID: 31175890.

Choi N, Ahn J, Cho YS. Taste Changes in Patients With Middle Ear Surgery by Intraoperative Manipulation of Chorda Tympani Nerve. Otol Neurotol. Jun. 2018;39(5):591-596. doi: 10.1097/MAO.0000000000001780. PMID: 29561383.

Ciofalo A, Zambetti G, Romeo M, Vestri AR, Iannella G, Re M, Magliulo G. Taste and olfaction in middle ear surgery. Ann Otol Rhinol Laryngol. Apr. 2015;124(4):312-6. doi: 10.1177/0003489414555900. Epub Oct. 30, 2014. PMID: 25358610.

Seaberg RM, Chadha NK, Hubbard BJ, Gordon KA, Allemang BA, Harrison BJ, Papsin BC. Chorda tympani nerve function in children: relationship to otitis media and body mass index. Int J Pediatr Otorhinolaryngol. Dec. 2010;74 (12):1393-6. doi: 10.1016/j.ijporl.2010.09.016. Epub Oct. 6, 2010. PMID: 20932587.

Stillman JA, Morton RP, Hay KD, Ahmad Z, Goldsmith D. Electrogustometry: strengths, weaknesses, and clinical evidence of stimulus boundaries. Clin Otolaryngol Allied Sci. Oct. 2003;28(5):406-10. doi: 10.1046/j.1365-2273.2003.00729.x. PMID: 12969341.

Ellegård EK, Hay KD, Morton RP. Is electrogustometry useful for screening abnormalities of taste? J Laryngol Otol. Dec. 2007;121(12):1161-4. doi: 10.1017/S0022215107000862. Epub Oct. 12, 2007. PMID: 17931447.

Antoli-Candela F Jr, Stewart TJ. The pathophysiology of otologic facial paralysis. Otolaryngol Clin North Am. Jun. 1974;7(2):309-30. PMID: 4599259.

Saito T, Ito T, Ito Y, Manabe Y, Sano K. Relationship between gustatory function and average number of taste buds per fungiform papilla measured by confocal laser scanning microscopy in humans. Eur J Oral Sci. Feb. 2017;125 (1):44-48. doi: 10.1111/eos.12329. PMID: 28084686.

PCT International Search Report and Written Opinion for International Application No. PCT/IL2022/050329, mailed Oct. 20, 2022, 9pp.

* cited by examiner

ELECTROPHYSIOLOGICAL DEVICE AND METHOD FOR DIAGNOSIS OF ACUTE UNILATERAL OTITIS MEDIA (AOM)

CROSS-REFERENCE TO RELATED APPLICATIONS

This application a National Phase of PCT Patent Application No. PCT/IL2022/050329 having International filing date of Mar. 24, 2022, which claims the benefit of priority of U.S. Provisional Patent Application No. 63/165,836, titled "ELECTROPHYSIOLOGICAL DEVICE AND METHOD FOR DIAGNOSIS OF ACUTE UNILATERAL OTITIS MEDIA (AOM)", filed Mar. 25, 2021, the content of which are all incorporated herein by reference in their entirety.

BACKGROUND OF THE INVENTION

Acute Otitis Media (AOM) is the most common bacterial infectious disease in children worldwide and is the leading cause of antibiotic treatment for children in developed countries. Existing AOM diagnostic methods have low specificity, while approximately only 40% of cases are diagnosed correctly. It is difficult to distinguish between AOM, which requires antibiotic treatment, and Otitis Media with Effusion (OME), that does not require antibiotic treatment. Therefore, the inaccuracy of AOM diagnosis results in an overdiagnosis of AOM and overuse of antibiotics, that enhances antibiotic resistance (a growing global threat) and promotes the post antibiotics-era. The main problem of existing AOM diagnostics tools is the lack of sufficient specificity.

Acute otitis media (AOM) is an inflammation of the middle ear and among the most common diseases in young children. The pathophysiology is multifactorial, and can result in complications, such as conductive hearing loss, tympanic nerve perforation, mastoiditis, meningitis, sinus vein thrombosis, and facial nerve paralysis. Acute facial nerve paralysis is a rare complication, and there are several hypotheses regarding its specific pathophysiology, such as direct involvement of the facial nerve by infection, facial nerve infarcts due to inflammatory edema, and demyelination of nerve fibers by bacterial toxins. The chorda tympani nerve (CTN) is a branch of the facial nerve which passes through the middle ear. It carries afferent special sensory fibers from the anterior two-thirds of the tongue and efferent parasympathetic innervation to the submandibular ganglion which innervates the submandibular and the sublingual glands. Middle ear inflammation during AOM is likely to affect the conductance and function of the CTN by means of the same mechanisms of acute facial nerve paralysis. Moreover, there is evidence for dysfunction of nerves which pass through an inflammatory environment.

CTN dysfunction has been reported in chronic otitis media and other pathologies of the ear, nose, and throat, but there have not been any publications on CTN involvement in AOM. In order to find a way of distinguishing AOM cases from other cases such as OME, a study was conducted to investigate CTN function in AOM patients aiming to take advantage of the phenomenon that CTN dysfunction, as measured by changes in gustatory thresholds, will be greater in the presence of middle ear inflammation in AOM.

AOM involves nerve damage that is associated with taste impairment, which can be detected using EEG electrodes and taste stimulation.

SUMMARY OF THE INVENTION

Aspects of the present invention may include a medical system for automatically measuring taste threshold for the diagnosis of a unilateral AOM. Taste sensation can be examined using electrogustometer (EGM) that a) stimulates the tongue using electrodes and b) measures taste threshold in an individual. The system may include patch electrodes to measure EEG response to these stimuli.

According to some embodiments the EGM may be combined with a disposable pacifier. In some embodiments, each side of the patient's tongue may be examined using the electrogustometer electrodes integrated in both sides of the pacifier, thus determining patient's bilateral taste threshold. In some embodiments, by analyzing taste thresholds, a diagnosis of a unilateral AOM may be achieved.

In some embodiments, a method of diagnosis of AOM may comprise: placing a monopolar probe on a first predefined location of a subject's tongue in a territory innervated by a chorda tympani nerve (CTN) associated with a first ear; applying a stimulus in a first strength by the monopolar probe to the first predefined location; measuring a response to the stimulus; changing the strength of the stimulus applied by the monopolar probe to the first predefined location based on the measured response until the measured response reaches a threshold value; determining a first stimulus strength at the threshold value for the first predefined location; repeating steps mentioned herein above for a second predefined location of the subject's tongue in a territory innervated by the CTN associated with a second ear, to determine a second stimulus strength at the threshold value for the second predefined location; and diagnosing AOM based on a resulting difference between the determined first and second stimulus strengths for the first and second locations.

In some embodiments, said stimulus is in a strength ranging between −6 dB and 32 dB. In some embodiments, said stimulus duration is between 200 and 1000 milliseconds.

In some embodiments, said monopolar probe is a 5 square millimeter electrode. In some embodiments, said first location is approximately 1.5 cm lateral to midline and approximately 1.5 cm proximal from a tongue tip from a first side of the subject's tongue. In some embodiments, said second location is approximately 1.5 cm lateral to midline and approximately 1.5 cm proximal from a tongue tip from a second side of the subject's tongue. In some embodiments, said first and second thresholds are determined based on electroencephalogram (EEG) measurements received during stimulation.

Some aspects of the present invention are directed to a system capable of diagnosing AOM, the system may include: an electrogustometer (EGM) comprising at least one monopolar probe; and an electroencephalogram (EEG) unit, configured to measure a response to the stimulus, and send a signal to the EGM based on the measured stimulus response. In some embodiments, the at least one monopolar probe of the EGM may include at least two electrodes.

In some embodiments, the EGM comprised in the system may be configured to apply a stimulus in a strength ranging between −6 dB and 32 dB. In some embodiments, said EGM may be configured to apply a stimulus for a duration between 200 and 1000 milliseconds. In some embodiments, said EGM may be configured to apply a stimulus until a measured response of the EEG reaches a threshold value.

In some embodiments, the at least one monopolar probe comprised in the EGM is a 5 square millimeter electrode.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
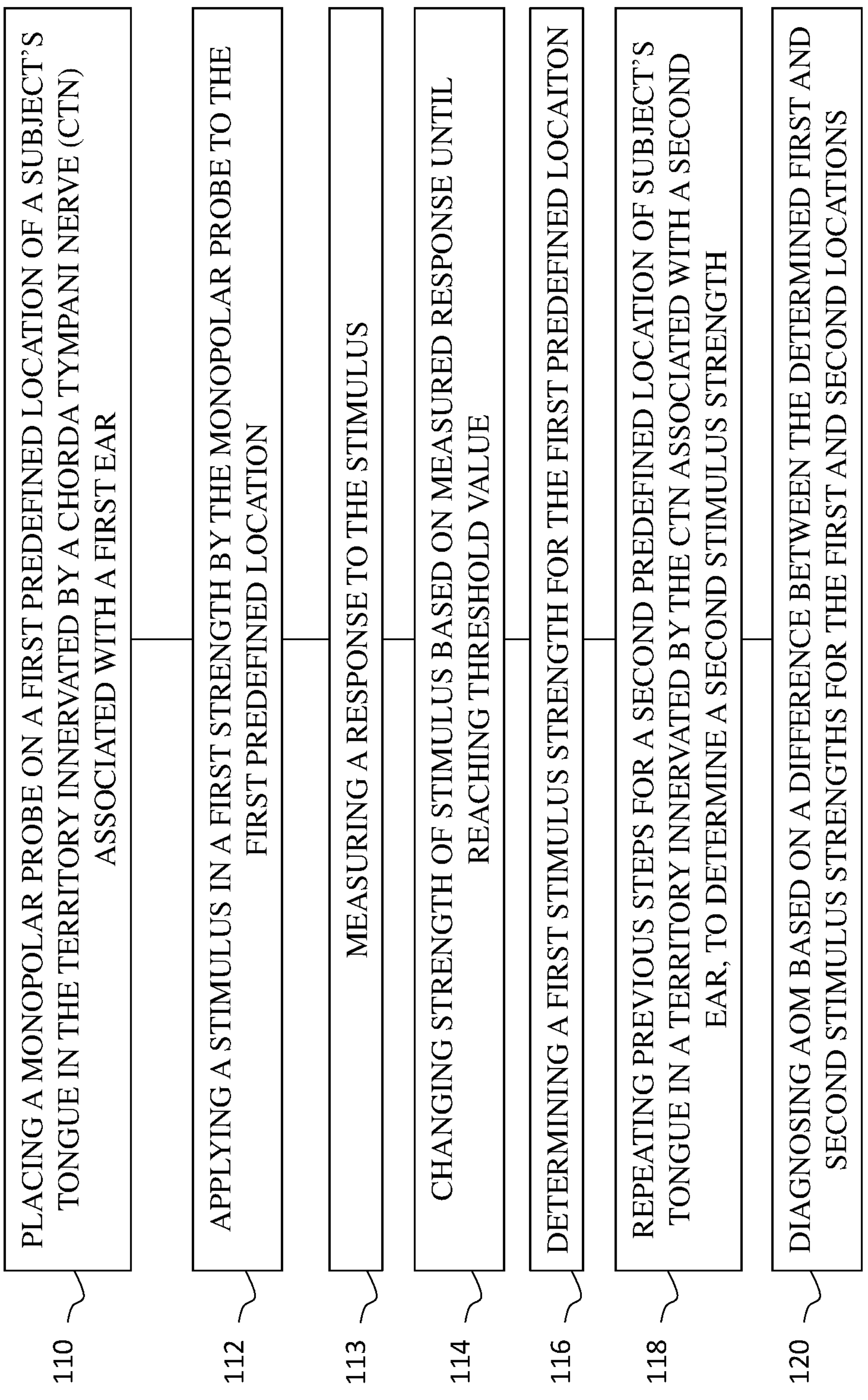
FIG. 1 is a flowchart of a method of diagnosis of AOM using electrophysiological properties according to some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

According to some embodiments of the present invention chorda tympani nerve (CTN) function may be measured by unilateral increases of gustatory thresholds in the presence of ipsilateral acute otitis media (AOM). Clinical study according to embodiments of the invention was conducted in patients of all ages with unilateral AOM. The study involved Electrogustometric examinations that were performed to evaluate the taste thresholds of each side of the tongue of each patient during an acute episode of unilateral AOM.

The terms of the electrogustometric examinations were: eleven consenting patients were initially recruited into the study, and ten patients aged (mean±standard deviation) 26.1±11.2 years comprised the final study group. Taste thresholds were significantly elevated on the side ipsilateral to the ear affected by AOM ($P<0.05$). Based on the examinations it was concluded that CTN conductance is impaired during the acute stage of AOM. In the examinations the CTN function was assessed in unilateral AOM. Electrogustometry examinations enabled determination of the bilateral taste thresholds during inflammatory states. Further, it was found that taste sensation on the ipsilateral side of the tongue decreased during acute episodes.

A clinical trial aiming to establish the above-described phenomena was performed in the emergency room (ER) of the Otolaryngology Head and Neck Surgery Department in the Tel Aviv Medical Center, Israel. Patients were recruited during their acute care visit in the ER and were asked to arrive to the outpatient clinic on the following day. Consenting patients that were diagnosed in the ER with unilateral AOM were recruited for participation in this study. Chart reviews were conducted to extract the following information: age, sex, smoking history, history of ear surgery, past medical history, and history of any issues or concerns with taste function. Eligible patients were those aged 6-40 years who were able to cooperate with and consent to the experimental procedure. Patients with a history of chronic otitis media, gustatory dysfunction, head and neck trauma or pathologies, as well as pregnant women were excluded.

The patients who had been diagnosed as having unilateral AOM within the past 48 hours were contacted and invited to participate in the study. First, the inflammatory AOM diagnosis was validated as still being in an active state by an otolaryngologist's examination that included otomicroscopy, and then bilateral electrogustometric (EGM) threshold measurements were performed by the investigators.

Aspects of the present invention are directed to an electrophysiological system and a method for diagnosis of acute otitis media (AOM). According to some embodiments, an electrophysiological system comprising an electrogustometer (EGM) may apply a stimulus onto a subject's tongue, which may result in a significant response from an electroencephalogram (EEG) comprised in the system determining whether the subject reaches a taste threshold at said stimulus. In some embodiments, the difference in taste thresholds based on applied stimulus strengths in different locations may determine a diagnosis of AOM.

Figure 2A:
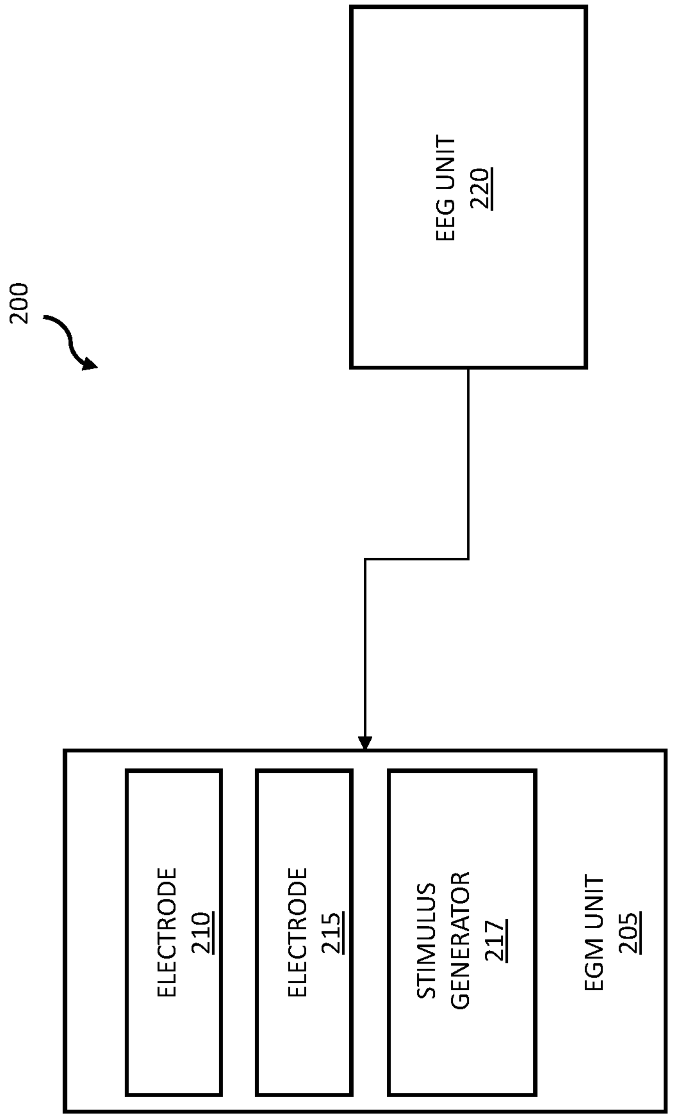
FIG. 2A is a block diagram of a system for diagnosis of AOM according to some embodiments of the invention.
Figure 2B:
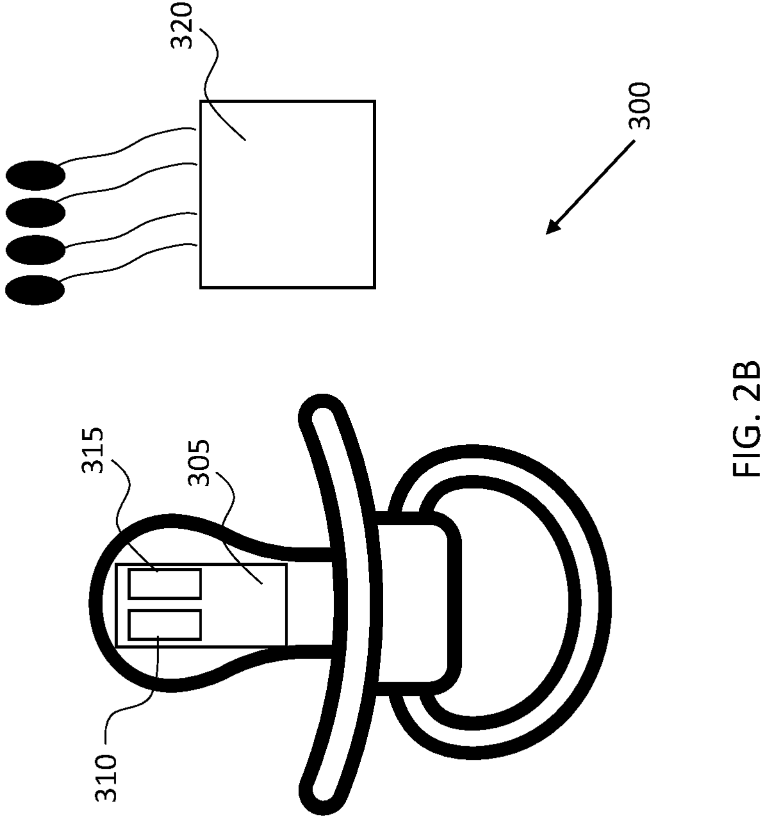
FIG. 2B is a schematic illustration of a device according to embodiments of the present invention.

Reference is now made to FIG. 1 which is a flowchart of a method of diagnosis of AOM according to some embodiments of the present invention. In step 110 a monopolar probe of an EGM device (e.g., as illustrated in FIGS. 2A and 2B) may be placed on a first predefined location of a subject's tongue in a territory innervated by a CTN, ipsilateral to a first ear of the subject. In Step 112, a stimulus may be applied to the first location at a first strength. The strength of the stimulus may range from, for example, −6 dB to 34 dB, −6 dB to 1 dB, 1 to 10 dB, 10 to 20 dB, 20 to 34 dB and any range and value herein between, and the stimulus duration may be 200-1000 milliseconds, 200-500 milliseconds, 500-700 milliseconds, 700-1000 milliseconds and any range and value herein between.

In step 113, a response to the stimulus may be measured. In some embodiments, the stimulus may be measured by an EEG configured to record a response from the subject. In some embodiments, said EEG may be placed in proximity to a first ear of the subject in order to measure said response.

In step 114, an EEG waveform analysis (e.g., Evoked-Related Potentials, ERP) may be conducted to evaluate the measured EEG response. In some embodiments, said EEG waveform analysis may indicate that in order to initiate a taste sensation, a change in stimulation strength is required and send a signal to the EGM to change a strength of the stimulus until reaching a waveform response which represents taste sensation (also referred to as "taste threshold"). In some embodiments, a decision to change stimulus strength may comprise comparing the measured EEG response to an ERP signal morphology, as discussed hereinbelow with respect to step 116.

In step 116, a first stimulus strength may be determined as a stimulus strength which represents taste sensation, based on the EEG waveform analysis of the first ear as a result of different stimulus strength from the first predefined location. In some embodiments, in order to qualify a measured response from the EEG as achieving a taste threshold at the first stimulus strength, a certain ERP signal morphology (as further detailed hereinbelow) may be compared to the measured EEG response. In some embodiments, said ERP signal morphology may be received from an external device associated with the EEG. In some embodiments, if said ERP signal morphology matches the waveform of the measured EEG response, said EEG response is recorded as a taste threshold at the first stimulus strength. In some embodiments, a non-limiting example of a comparable ERP signal morphology includes P1-N1-P2, wherein P1 represents a first observed positive peak of a signal, N1 represents a first observed negative peak of said signal, and P2 represents a second observed positive peak of said signal. In some embodiments, if said measured EEG response does not match the received ERP signal morphology, a stimulus strength may be further changed, as discussed hereinabove with respect to step 114.

In step 118, the previous steps mentioned herein above may be repeated for a second predefined location of the subject's tongue in a territory innervated by the CTN ipsilateral to a second ear of the subject, to determine a second stimulus strength. It should be appreciated that the order of steps may be changed and that some of the steps may be conducted simultaneously or in parallel.

Finally, in step 120, unilateral AOM may be diagnosed based on difference between the determined stimulus strengths for the first and second ears. For example, unilateral AOM may be determined when the stimulus strength determined for one ear is significantly higher than for the other ear, as further evident in the experimental results provided in FIGS. 3A and 3B.

Reference is now made to FIG. 2A which is a block diagram of a system 200 for performing AOM diagnosis according to some embodiments of the present invention. Device 200 according to some embodiments of the present invention may include an electrogustometer (EGM) unit 205 comprising electrodes 210 and 215. In some embodiments, electrodes 210 and 215 may stimulate portions of a tongue of patient. In some embodiments, an EEG unit 220 may detect a signal from the patient, wherein said EEG unit 220 may further send a signal to a stimulus generator 217 of EGM unit 220, to change a stimulation strength of the tongue of patient. According to some embodiments, the stimulation strength may be changed until a signal from EEG unit 220 is received, indicating that a threshold value has been reached. According to some embodiments, the change in stimulation strength may be a decrease in the stimulation and the indication from EEG unit 220 may be provided when the signal detected by EEG unit 220 is below a threshold value. According to other embodiments, the change in stimulation strength may be an increase in the stimulation and the indication from EEG unit 220 may be provided when the signal detected by EEG unit 220 is above a threshold value.

Reference is now made to FIG. 2B which is an illustration of a device 300 for AOM diagnosis according to one embodiment of the present invention. Device 300 may include an electrogustometer (EGM) unit 305 and an EEG unit 320. EGM unit 305 may include electrodes 310 and 315 to stimulate portions of a tongue of a patient (or subject). Electrodes 310 and 315 may be monopolar probes and may be configured to apply a stimulus in the range of, for example, −6 dB to 34 dB for a duration of up to, for example, 500 ms.

According to some embodiments, EGM unit 305 may be enclosed or included in a pacifier as illustrated in FIG. 2B.

In some embodiments, device 200 or 300 may be used to perform the method of diagnosis of AOM mentioned herein above. In some embodiments, device 200 or 300 is capable of applying a stimulus in a first strength to a first predefined location, determining a first stimulus strength, applying a stimulus to a second predefined location, and determining a second stimulus strength as discussed herein above. In some embodiments, device 200 or 300 may stimulate a tongue of a patient or subject in a plurality of locations, to receive an EEG response. In some embodiments, device 200 or 300 is capable of stimulating a tongue of a patient or subject via at least one electrode comprised in EGM unit 205 or 305, respectively.

In some embodiments, EGM unit 205 or 305 of device 200 or 300 is configured to send a signal to EEG unit 220 or 320, respectively. In some embodiments, said signal may contain a taste threshold value, said threshold value received by stimulating a tongue of a patient or subject. In some embodiments, EEG unit 220 or 320 may further send a signal to EGM unit 205 or 305 in order to change a strength of said stimulus. In some embodiments, EGM unit 205 or 305 may direct electrodes, comprised in said EGM unit, to stimulate a tongue of a patient or subject in a second strength based on received signal from EEG unit 220 or 320, respectively. In some embodiments, a stimulus of patient or subject by EGM units 205 or 305 may be repeated in a plurality of locations of said patient or subject's tongue, to determine a plurality of stimulus strengths.

Clinical Trial

A clinical trial was performed according to embodiments of the invention discussed herein above for diagnosing AOM. CTN function was assessed by determining the taste threshold, and EGM analysis was performed with a RION TR-06 electrogustometer (Sensonics Inc., Haddon Heights, NJ). The stimulus was applied by placing a 5 mm monopolar probe 1.5 cm lateral to midline and 1.5 cm proximal from the tongue tip in the territory innervated by the CTN. The strength of the stimulus ranged from −6 dB to 34 dB, and the stimuli duration was 500 ms. Both sides of the tongue were tested separately, with the healthy side tested first. Two alternative forced choice paradigms were performed, with alternating increasing and decreasing stimulus strength within a staircase paradigm. The turning point was defined as two correct answers or one incorrect answer, leading to an increase or decrease, respectively, of stimulus strength. The taste threshold was the average of the last four turning points. The resulting taste thresholds are further discussed herein below with reference to FIGS. 3A and 3B.

Statistical Analysis

The statistical analyses were performed with MATLAB (2018A, MathWorks). The one-tailed paired t-test was used to compare taste thresholds between the healthy and the affected sides. The significance level was set at $P<0.05$.

Experimental Results

Figure 3B:
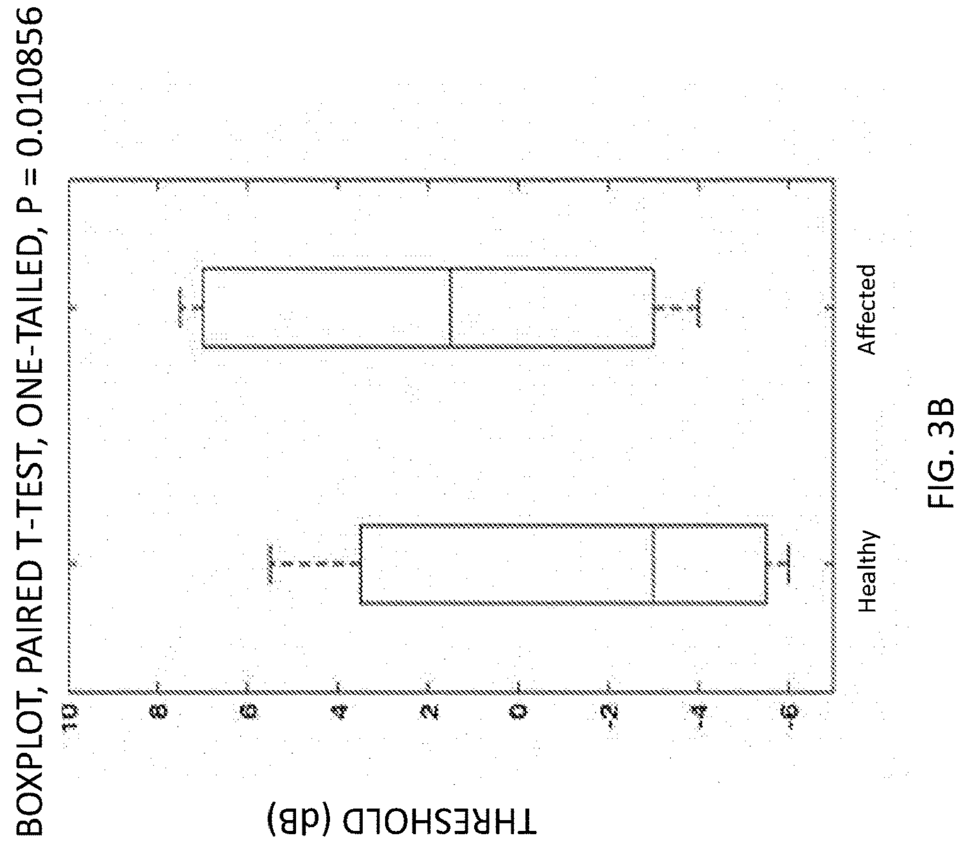
FIGS. 3A and 3B are diagrams showing experimental data of taste thresholds in AOM.
Figure 3A:
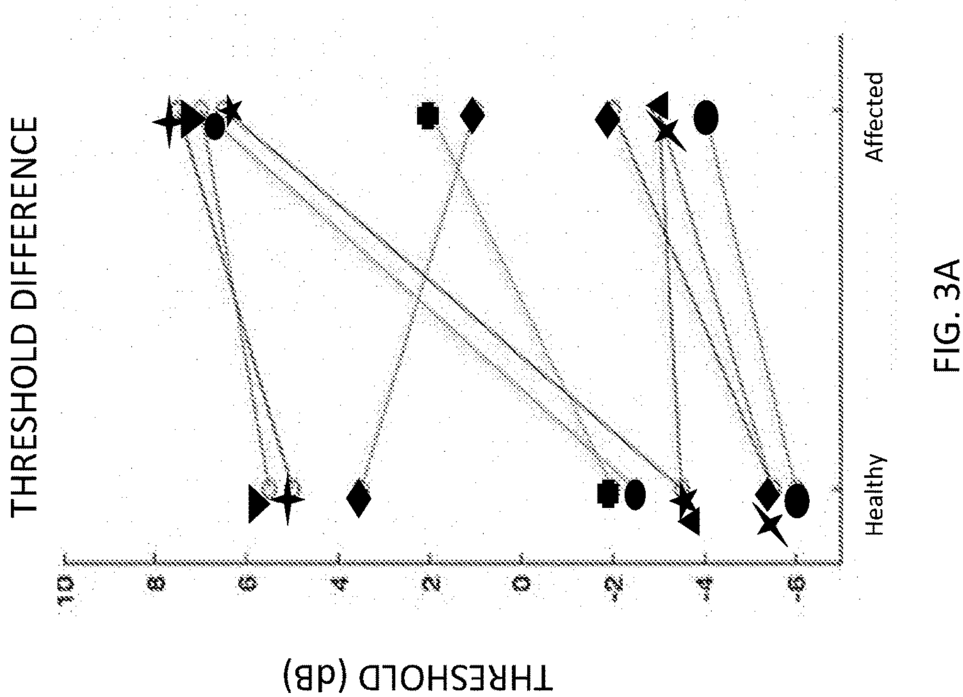

Reference is now made to FIGS. 3A and 3B showing experimental data of taste thresholds in AOM as received from a study discussed herein below. A total of 11 participants were recruited to the study, and one patient was dropped due to active smoking. The ten suitable patients with inflammatory unilateral AOM included nine females and one male whose mean age±standard deviation was 26.1±11.2 years. One patient also had mild external otitis ipsilateral to the study ear, one also had acute mastoiditis ipsilateral to the study ear, and one also had serous otitis media contralateral to the study ear. Comparison of the taste threshold in the AOM-affected side (mean 1.9±4.75) to the healthy side (mean −1.45±4.44) revealed a significant increase in taste threshold on the affected side ($P<0.05$). FIG. 3A presents the taste thresholds per patient per side.

Each patient is represented by a single line, when the left column represents the healthy side, and the right column represents the affected side (AOM). FIG. 3B presents a boxplot of taste thresholds in both the affected and healthy sides, performed through a one-tailed paired t-test as described herein above using MATLAB, with $P<0.05$. In both FIGS. 3A and 3B, the vertical axis represents a resulting taste threshold in dB for each side of the patient's tongue as discussed herein above.

DISCUSSION

The effect of AOM on chorda tympani nerve function has not been studied in depth in the past. This study employed an EGM methodology in order to evaluate the taste thresholds of each side of the tongue of patients with verified unilateral inflammatory AOM. The principal finding was a unilateral increase in EGM tracings of gustatory thresholds on the affected side during the inflammatory phase of AOM. This heretofore unreported association has possible implications on the understanding of the pathophysiology of acute infection on CTN conductance as well as on the diagnosis of AOM.

Previous studies have shown the effect of chronic ear infection and otologic surgery on CTN function. However, the current study appears to be the first to address the effect of middle ear inflammation in the setting of AOM on gustatory thresholds during the acute phase of disease.

The strengths of this study are that the measurements were performed during the acute phase of infection and that they revealed a significant increase in the EGM thresholds on the side ipsilateral to the affected ear. The weaknesses of the study are related to the study population's having an average age of 26 years, which does not reflect the pediatric age group that is most affected by AOM. This was the result of reduced ability of younger children to complete EGM examinations, as showed by Leung et al.[10]. Moreover, both the adult and pediatric patients were recruited during their acute care visit in the ER and they were asked to arrive to the outpatient clinic on the following day. The lack of compliance for the return visit was mostly on the part of the parents of the suitable children. Nevertheless, the pathophysiology of acute inflammation in the middle ear with resulting reduction of CTN conductance among adults should not be fundamentally different from those in younger age groups, and these results can be extrapolated to apply to children. Another limitation is the relatively small cohort of ten patients and the use of EGM technology which is operator-dependent and has low sensitivity.

Figure 4A:
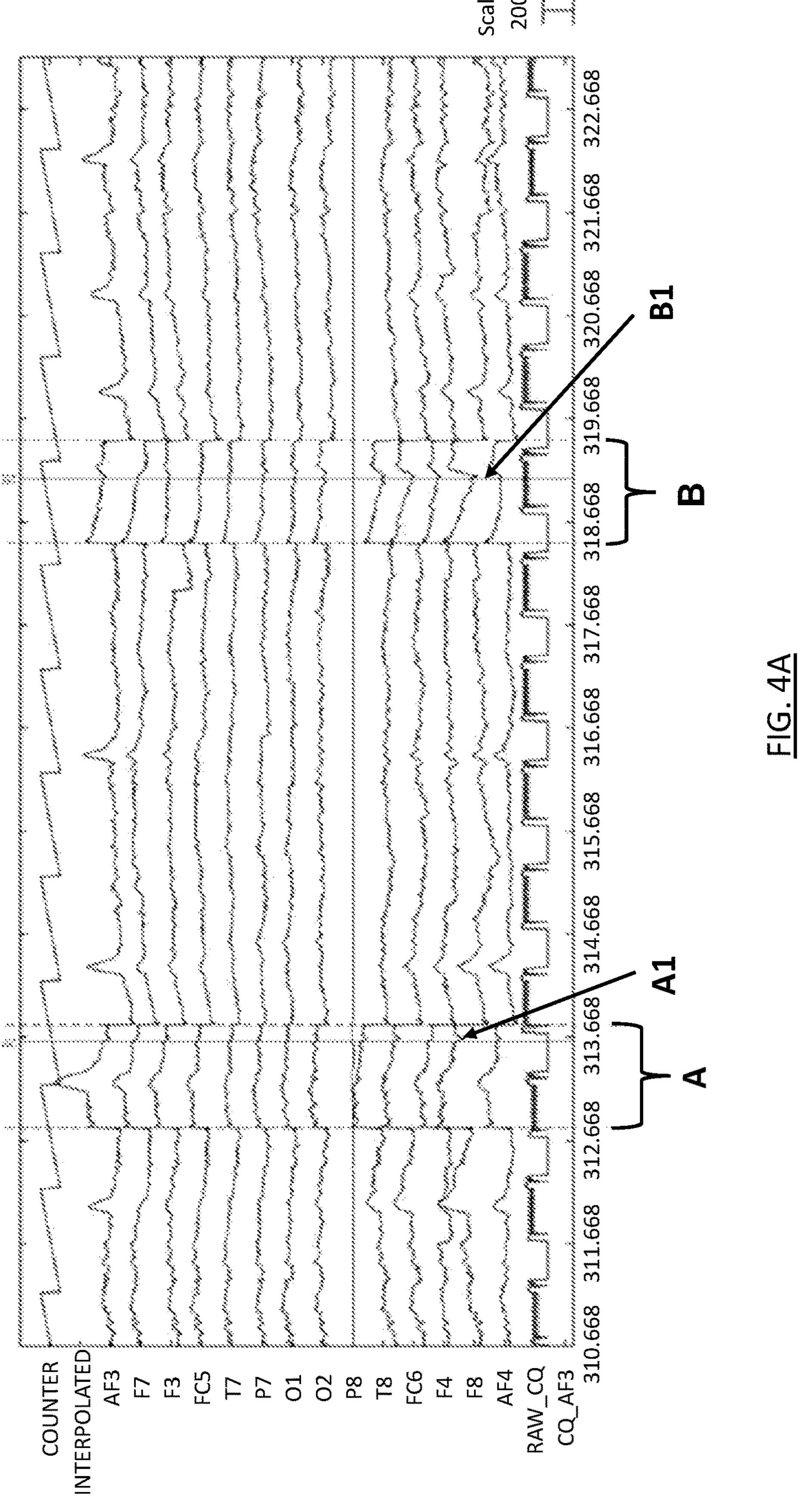
FIGS. 4A and 4B are diagrams showing experimental data of measurements of EEG in response to EGM.
Figure 4B:
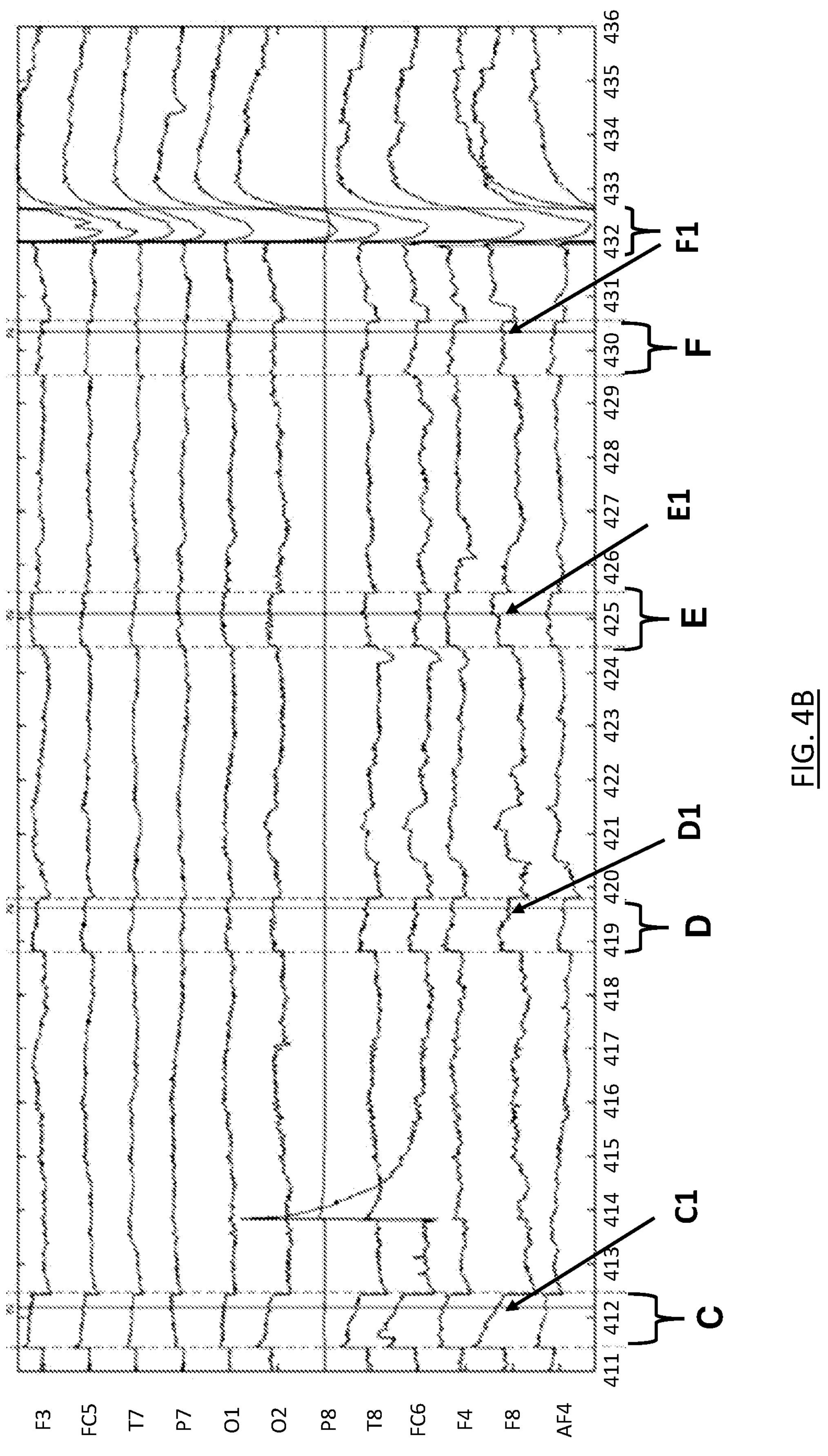

With reference to FIGS. 4A and 4B, initial measurements of EEG in response to EGM are demonstrated. FIG. 4A details an experimental stimulation of an EEG response to EGM stimulation of a subject according to some embodiments of the invention, where the horizontal axis represents time, and vertical axis represents an EEG voltage response across 14 EEG channels separated vertically. Portions A and B of FIG. 4A show a 1 second stimulation of 20 μA, with a recorded sense event reflected in the EEG response at locations A1 and B1, respectively. Subject's EEG response of EGM stimulation can be shown as a sharp response in EEG levels as a result of EGM stimulation.

FIG. 4B details an experimental stimulation of an EEG response to EGM stimulation of a subject according to some embodiments of the invention, where the horizontal axis represents time, and the vertical axis represents an EEG voltage response across 14 EEG channels separated vertically. Portions C, D, E, and F show a 1 second stimulation of 20 μA. Marked locations C1, D1, E1, and F1 show a recording reported by the subject, of taste sensation. As the subject's tongue is stimulated via the EGM, a measured response by the EEG is observed, in addition to the subject reporting a taste sensation.

As may be understood from FIGS. 4A and 4B, a taste sensation occurs during EGM stimulation of a subject as recorded by an EEG. In some embodiments, an EEG recording as illustrated in FIGS. 4A and 4B may be analyzed according to some embodiments of the invention, for example, to diagnose AOM in the subject. A diagnosis of AOM may be presented by performing aspects of the present invention, for example, by analyzing waveforms of EEG channels during stimulation to determine stimulus strengths at separate locations wherein a taste sensation occurs. An EEG recording, for example, the EEG responses illustrated in FIGS. 4A and 4B, may be compared to an ERP signal morphology as described hereinabove to determine whether a stimulus by the EGM achieves a taste sensation in the subject at a given stimulus strength. By analyzing the EEG response in a first and second location of a subject's tongue until taste sensations occur, a first and second stimulus strength may be determined. In some embodiments, by analyzing the waveform response of an EEG to determine stimulus strengths in first and second locations where an EGM stimulus is applied, and comparing the differences between said stimulus strengths, a diagnosis of AOM may be presented.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of diagnosis of unilateral Acute Otitis Media (AOM), the method comprising:

a. placing (110) a monopolar probe on a first predefined location of a subject's tongue in a territory innervated by a chorda tympani nerve (CTN) associated with a first ear;

b. applying (112), by an Electrogustometer (EGM) unit, a stimulus in a first strength by the monopolar probe to the first predefined location;

c. measuring (113), by an electroencephalogram (EEG) unit, a response to the stimulus;

d. changing (114), by the EGM unit, the strength of the stimulus applied by the monopolar probe to the first predefined location based on the measured response until the measured response reaches a threshold value;

e. determining (116), by the EEG unit a first stimulus strength at the threshold value for the first predefined location;

f. repeating (118) steps a-e for a second predefined location of the subject's tongue in a territory innervated by the CTN associated with a second ear, to determine a second stimulus strength at the threshold value for the second predefined location; and g. diagnosing (120) unilateral AOM based on a difference between the determined first and second stimulus strengths for the first and second locations.

2. The method according to claim 1 wherein the stimulus is in a strength ranging between-6 dB and 32 dB.

3. The method according to claim 1, wherein the stimulus duration is between 200 and 1000 milliseconds.

4. The method according to claim 1, wherein the monopolar probe is a 5 square millimeter electrode.

5. The method according to claim 1, wherein the first location is about 1.5 cm lateral to midline and about 1.5 cm proximal from a tongue tip from a first side of the subject's tongue.

6. The method according to claim 1, wherein the second location is about 1.5 cm lateral to midline and about 1.5 cm proximal from a tongue tip from a second side of the subject's tongue.

7. The method according to claim 1, wherein the thresholds are determined based on electroencephalogram (EEG) measurements received during stimulation.

8. A system for diagnosing unilateral AOM, comprising:

an electrogustometer (EGM) comprising at least one monopolar probe configured to apply a stimulus to a subject, and an electroencephalogram (EEG) unit, configured to:

a. measure a response to the stimulus, and b. send a signal to the EGM based on the measured stimulus response.

9. The system of claim 8, wherein the at least one monopolar probe comprises at least two electrodes.

10. The system according to claim 8, wherein the EGM is configured to apply a stimulus in a strength ranging between-6 dB and 32 dB.

11. The system according to claim 8, wherein the EGM is configured to apply a stimulus for a duration between 200 and 1000 milliseconds.

12. The system according to claim 8, wherein the at least one monopolar probe is a 5 square millimeter electrode.

13. The system according to claim 8, wherein the EGM is configured to apply a stimulus on a subject's tongue, wherein a first location of the stimulus is about 1.5 cm lateral to midline and about 1.5 cm proximal from a tongue tip from a first side of the subject's tongue.

14. The system according to claim 13, wherein a second location of the stimulus is about 1.5 cm lateral to midline and about 1.5 cm proximal from a tongue tip from a second side of the subject's tongue.

15. The system according to claim 8, wherein the EGM is configured to apply a stimulus until a measured response of the EEG reaches a threshold value.

* * * * *